United States Patent [19]

Reichenberger

[11] 4,041,933
[45] Aug. 16, 1977

[54] ELECTRODE FOR POLAROGRAPHIC MEASUREMENTS IN PHYSIOLOGICAL MEDIA

[75] Inventor: Helmut Reichenberger, Brand, Germany

[73] Assignee: Siemens Aktiengesellschaft, Berlin & Munich, Germany

[21] Appl. No.: 567,175

[22] Filed: Apr. 11, 1975

[51] Int. Cl.² ............................................. A61B 5/04
[52] U.S. Cl. ................................. 128/2 E; 204/195 P
[58] Field of Search ................... 128/2 E, 2 L, 2.1 E; 204/195 B, 195 P

[56] References Cited

U.S. PATENT DOCUMENTS 3,912,614  10/1975  Spracklen et al. ............... 204/195 P

OTHER PUBLICATIONS

"Catheter-Mounted Oxygen Electrode for Monitoring Oxygen Tension" by S. Shinmaru et al, from the Periodical Cardiovascular Research Center Bulletin; Apr.--June 1972, pp. 111–122.

"The Measurement of Oxygen Tension in Tissues" by I. A. Silver, from the Symposium on Oxygen Measurement in Blood and Tissues and Their Significance; Churchill, Ltd., London, 1966, pp. 135–153.

Primary Examiner—William H. Grieb
Attorney, Agent, or Firm—Hill, Gross, Simpson, Van Santen, Steadman, Chiara & Simpson

[57] ABSTRACT

An electrode for effecting polarographic measurements in physiological media, in particular an oxygen electrode for the measurement of the partial pressure or tension of the oxygen in the human or animal body; encompassing a noble metal cathode which is sheathed by an insulating material, provided at the distal end thereof with a connector for an electrical power supply, as well as for an indicating and/or processing unit, and covered at the proximal end thereof with an oxygen-pervious, conductive membrane, as well as being conductively connected through the physiological medium with another anode. The noble metal cathode evinces the form of a piece of conductor cable having at least one noble metal wire, preferably gold wire, embedded in and extending through the insulating material, so as to provide a conductor wire. In a preferred embodiment of the invention, the noble metal cathode is constituted of a noble metal wire piece which is covered with an insulating lacquer, preferably a polyurethane.

24 Claims, 14 Drawing Figures

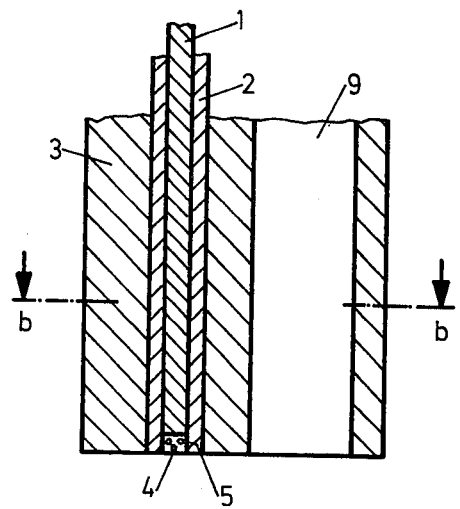
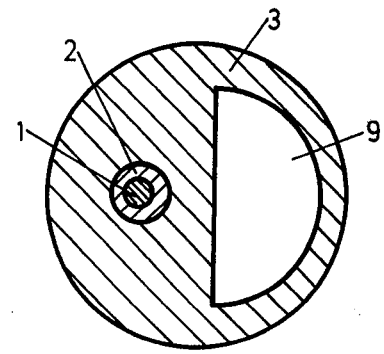
Fig.6a　　　　　　Fig.6b
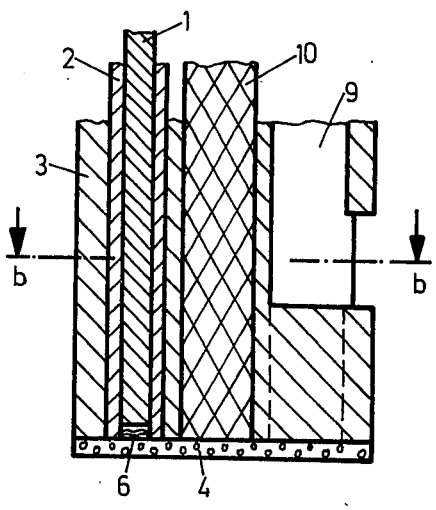
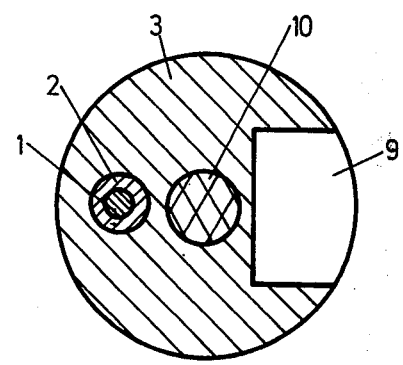
Fig.7a　　　　　　Fig.7b

ELECTRODE FOR POLAROGRAPHIC MEASUREMENTS IN PHYSIOLOGICAL MEDIA

FIELD OF THE INVENTION

The present invention relates to an electrode for effecting polarographic measurements in physiological media, in particular an oxygen electrode for the measurement of the partial pressure or tension of the oxygen in the human or animal body, encompassing a noble metal cathode which is sheathed by an insulating material, provided at the distal end thereof with a connector for an electrical power supply, as well as for an indicating and/or precessing unit, and covered at the proximal end thereof with an oxygen-pervious, conductive membrane, as well as being conductively connected through the physiological medium with another anode (in contrast with the so-called Clark electrodes, wherein noble metal electrodes and anodes lie in a common electrolyte chamber which is separated from the physiological medium by means of an oxygen-pervious electrically insulating membrane).

DISCUSSION OF THE PRIOR ART

Through the article "The Measurement of Oxygen Tension in Tissues" by I.A. Silver, from the symoposium on Oxygen Measurement in Blood and Tissues and their Significance; Churchill Ltd., London, 1966, page 135, there have already become known, for example, electrodes for measurements of the partial pressure of oxygen ($po_2$-measurements) in the brain, muscles and various body tissues, in which a short platinum or gold wire which is molten into a glass capillary is employed as the cathode, and which is drawn out to a tip having a diameter of a few $\mu m$ (3 to 10 $\mu m$) in a specialized operative process. The tip may then be covered with an oxygen-pervious membrane. The counterelectrode, mostly a chlorinated silver wire, is located in the tissue separately from the measuring electrode.

Furthermore, through the article "Catheter-Mounted Oxygen Electrode for Monitoring Oxygen Tension" by S. Shinmaru el al, from the periodical Cardiovascular Research Center Bulletin, April-June 1972, particularly page 112, there has become known another electrode of this type, in which the cathode is formed through a tiny gold piece applied to the tip of a steel wire. The steel wire and gold are hereby cast into an insulating material (epoxy cement), whereupon the casting mass additionally is sheathed with a further insulating layer formed of body-compatible material (Teflon). The proximal end of this electrode (gold tip) is covered with an oxygen-pervious membrane.

It is disadvantageous that these known electrodes evidence a relatively complicated and, additionally in the case of glass electrodes, a breakable construction. The complicated constructive embodiments cause considerable manufacturing difficulties as a result in multiplicity an complexity of the required individual mounting steps during the assembly of the electrodes which, overall, render the electrodes much more expensive, and prevent the inexpensive and simply mass production thereof.

SUMMARY OF THE INVENTION

Accordingly, it is an object of the present invention to provide an electrode of the above-mentioned type which, essentially, is constructed much simpler than the known electrodes, and which is thereby better suited than those for the problemless and inexpensive mass production, and with a good reproducibility of the electrode properties. The electrode in particular is usable for the undisturbed long-term supervision over the oxygen tension in the organism.

The foregoing object is inventively solved in that the noble metal cathode evinces the form of a piece of conductor cable having at least one noble metal wire, preferably gold wire, embedded in and extending through the insulating material, so as to provide a conductor wire.

In the electrode according to the invention, there is consequently utilized as the base material for the noble metal cathode, a simply producible (as continuously reeled-out or meter goods) noble metal wire-insulating cable from which the cathode may be cut-off piecemeal in, for example, a cutting operation. The thus obtained cable section pieces need then be merely convered proximally with the oxygen-pervious membrane, and distally soldered with the electrical connecting conduits for the electrical power supply, as well as indicator and/or processing unit soldered thereto or, for example, clamped together by means of a sleeve which is slid thereover. Thereby is constituted an electrode which is assemblable in a few simple operative steps, so as to be also inexpensive and particularly well suited for mass production thereof (at a good reproducibility of the electrode properties). Moderately priced electrodes may be employed as single-use articles for one-time use, and then discarded after utilization.

In a preferred embodiment of the invention, the noble metal cathode is constituted of a noble metal wire piece which is covered with an insulating lacquer, preferably a polyurethane. Should the already insulated noble metal cathode additionally also be sheathed or covered by a body-compatible insulating material, then in addition to the heretofore usual spraying on of body-compatible plastic material, there is also afforded a sheathing in a manner whereby the noble metal cathode is embedded between at least two foils formed of the additional insulating material, wherein the foils may then be intimately connected with each other through thermal welding, and subsequently pressed through thermal deformation or the like into, for example, a circular shape. Also this type of additional insulating merely requires a simple additional operative sequence, and thereby similarly affords the sought for goal in achieving the simple and inexpensive mass production of the electrodes.

Prior to the application of the oxygen-pervious membrane to the proximal end of the noble metal cathode, for the purpose of achieving a definite gold surface, this end should preferably be previously etched. Recommended hereby is that the etching sequence be carried out to such an extent, that the noble metal wire at the proximal end of the cathode is set back with respect to the insulating material, meaning, that a noble metal recess or groove is formed at the proximal end with respect to the insulating material. This metal recess may then be subsequently filled with an electrolyte, and only then is the recess covered with the membrane. The introduction of an electrolyte into the recess, in particular at suitable pulsating operation of the electrode, brings the advantage that the polarographic currents which occur during the measurement phase are less dependent upon the instantaneous diffusion properties of the membrane. At a lengthier deposition of the electrodes in a common salt solution, the electrolyte can also be filled with a physiological NaCl solution by means of diffusion through the porous membrane. The prefilling of the recess with electrolyte solution prior to the application of the membrane is thereby rendered superfluous.

The physical application of the inventive electrode in the body tissues may be carried out, for example, through the intermediary of an injection needle, in which the noble metal cathode has been introduced, and then injected by the needle syringe into the body tissues. In contrast therewith, for oxygen measurements directly in the blood vessels (veins), it is recommended that the electrode be constructed as a catheter and, through insertion of the catheter into the corresponding blood vessel, the catheter measurement tip be positioned at the desired measuring location. The counter electrode (anode) may, in both instances, be selectively applied on the body surface or in the physiological medium.

BRIEF DESCRIPTION OF THE DRAWINGS

Further advantages and details of the invention may be now ascertained from the following description of exemplary embodiments thereof, taken in conjunction with the accompanying drawings; in which:

FIGS. 6a to 9c illustrate an electrode pursuant to the invention constructed as a catheter, wherein the respective counter electrode is positionable either separately from the catheter in the blood, respectively, on the skill surface in proximity to the measuring location, or is located on the catheter, together with the cathode.

DETAILED DESCRIPTION

Referring now in detail to the drawings, in the electrodes according to FIGS. 1 through 4, utilized each time as the base material for the noble metal cathode is a circular cable piece, which consists of a gold wire 1, as well as of an insulating lacquer sheathing 2 constituted, for example, of polyurethane. The gold wire 1 hereby evinces a diameter in the magnitude of 10 to 100 $\mu$m, and preferably 60 $\mu$m. The pieces of the cathode base material are severed pieces of a lengthier continuously being produced gold wire-insulating cable (meter goods).

Figure 1:
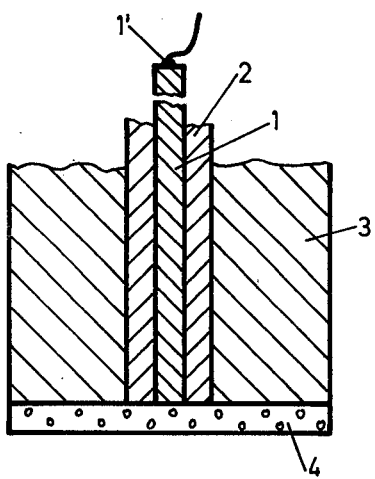
FIGS. 1 through 4 illustrate four different embodiments of a monopolar electrode constructed pursuant to the invention.

In the embodiment according to FIG. 1, the base cable peice 1, 2 is sheathed with an additional insulating compound 3 of body-compatible insulating material, for example, Teflon. The proximal end of the electrode hereby is etched along one plane, and on the edged surface there is applied an oxygen-pervious membrane 4. Coming into question as membrane material, there may preferably hereby be employed hydrophilic materials which are permeable only to small molecules and ions, but not however to macro molecules, for example, such as egg white, with the material, including wetted polymethacrylate, polystyrol or cellulose acetate. At the distal end of the gold wire 1 there is further connected the electrical connecting conduit 1' between the wire 1 and a power supply (not shown), as well as an indicator and/or processing unit, on the one hand, for the provision of the electrode potential, and on the other hand, for the measurement and the indication, or respectively processing, of the polarographic currents, by being soldered thereto or clamped thereon by means of a sleeve or jacket. This type of connection between the signal conduit 1' and the gold wire 1 is equally applicable to the collective further exemplary embodiments.

Figure 2:
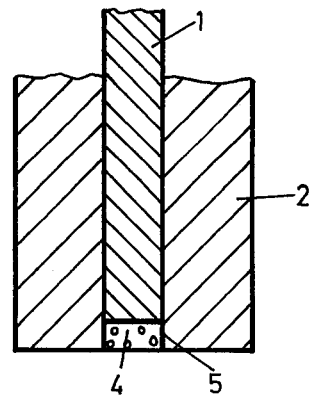
Figure 3:
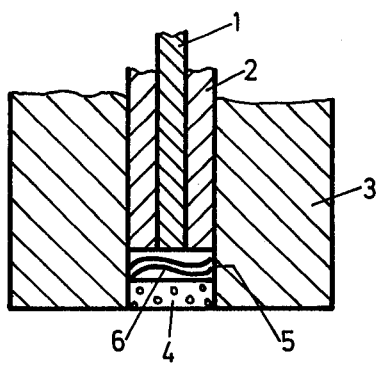
Figure 4:
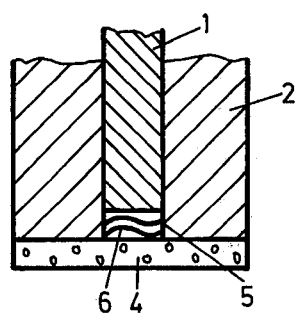

As distinct from the embodiment according to FIG. 1, in the embodiment of FIG. 2 there is formed a recess 5 at the proximal end of the cathode through subsequent etching out of gold with respect to the insulating material, into which there is then directed positioned the membrane 4. The embodiments pursuant to FIGS. 3 and 4 evidence corresponding recesses 5. In comparison with the embodiment according to FIG. 2, the embodiment of FIG. 3, however, includes also an electrolyte chamber 6 in the recess 5 between the gold wire 1 and the membrane 4. A corresponding electrolyte chamber 6 is also provided in the embodiment according to FIG. 4. In contrast with the other embodiments, the membrane 4 herein, however, is not placed into the recess 5 but, in correspondence with the embodiment of FIG. 1, again covers the entire distal end of the electrode. In correspondence with the embodiment according to FIGS. 1 through 3, the cathodes according to FIGS. 2 and 4 may naturally also be sheathed with an additional body-compatible insulating material, for example, Teflon.

Figure 5:
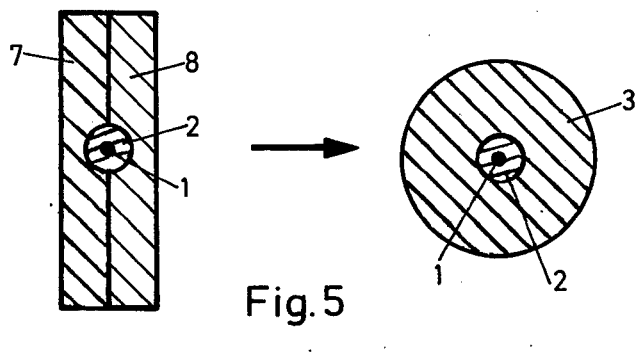
FIG. 5 illustrates the sheathing of an electrode constructed pursuant to the invention with an additional body-compatible insulating material in the major operating methods.
Figure 8:
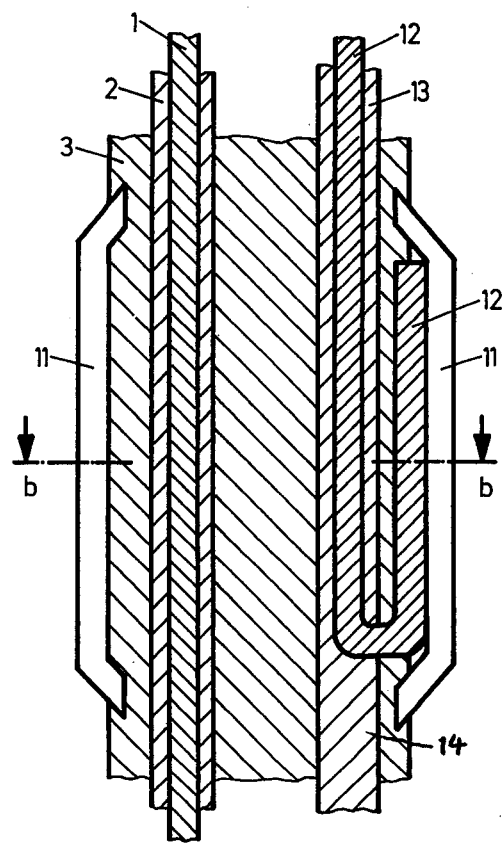
Figure 8:
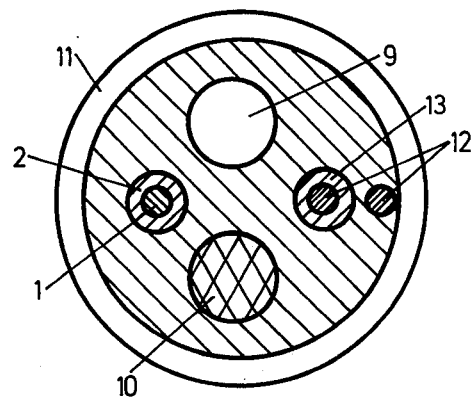

FIG. 5 shows, in section, again the sectional piece of the electrode base material with the gold wire 1 and the insulating lacquer 2. The wire cable piece 1, 2 hereby is inserted between plastic material foils 7 and 8 which, for example, are formed of Telfon. The foils at a width of approximately 500 $\mu$m, evidence a thickness of approximately 50 $\mu$m. The two foils 7, 8 are initmately thermally welded to each other at their contact surfaces. After welding they are then brough into a circular shape through heating and pressing. The additional body-compatible insulating material which is pressed into the circular shape corresponds to the additional plastic material sheathing 3 illustrated in FIGS. 1 and 3 of the drawings.

In the catheter constructions according to FIGS. 6a through 9c (catheter tips shown in longitudinal-and cross-sections) there the gold wires, insulating lacquer, as well as additional insulating material of the electrode (which here concurrently forms the catherter material), is again identified by the reference numerals 1, 2 and 3. Correspondingly, the membrane, as well as the electrolyte, are again designated by references numerals 4 and, respectively, 6.

Figure 9A:
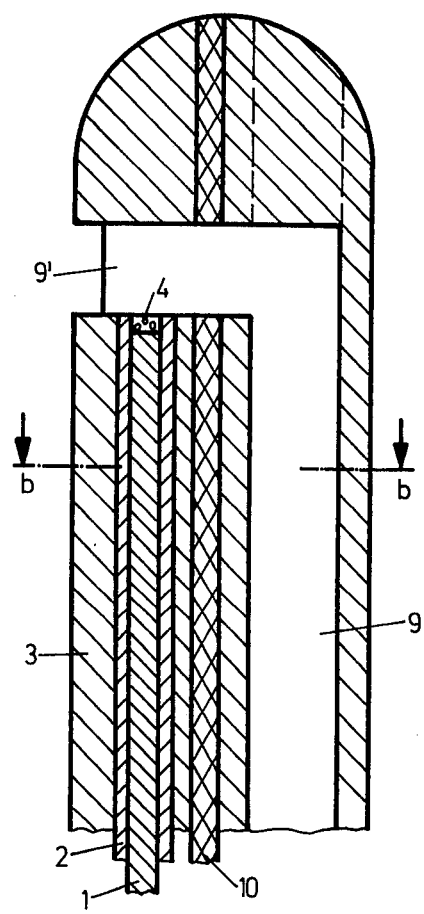
Figure 9B:
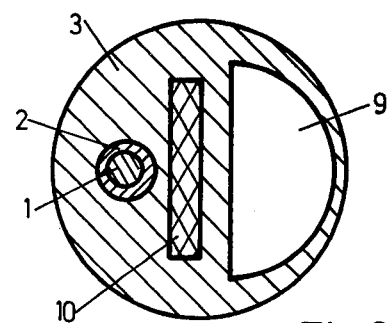
Figure 9C:
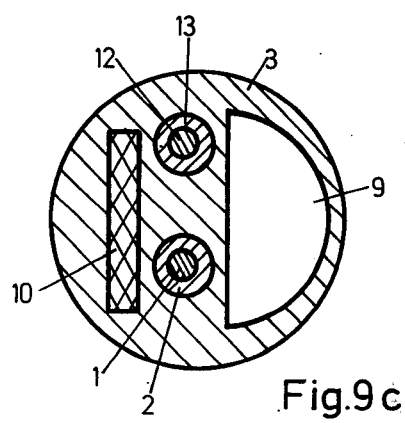

All of these forms of embodiments are further provided with a through channel 9 (lumen) in the catheter material which, in particular, serves for the additional withdrawal of blood-or tissue samples or, as for example, in the catheter construction pursuant to FIGS. 9a through 9c, also for the rinsing of the proximal oxygen electrode end with a rinsing medium, in particular an NaCl solution. In the embodiment according to FIGS. 6a, b, as well as 8a, b, the through channel 9 hereby terminates directly at the catheter tip adjacent the monopolar electrode 1, 2; and contrastingly in the embodiment forms according to FIGS. 7a, b and 9a through 9c, sideways ahead of the actual catheter tip. In addition, all of the catheters according to FIGS. 7a through 9c, for reinforcement of their tension strength, also include a high tensile textile core 10 (textile fiber).

The electrodes of the catheter according to FIGS. 6a through 7b, as well as 9a and 9b, jointly with a counter electrode, the latter of which, for example, is placed on the skin surface, in particular an Ag/Ag Cl-electrode (which, for example, may concurrently also serve for the withdrawal of further physiological measurement values, such as for example EKG or the like), will provide a simple unipolar measurement system for the oxygen tension.

A correspondingly simple bipolar measurement system is obtained through direct application of the counter electrode at the catheter. In the exemplary embodiment according to FIG. 8a, b, the counter electrode, for example, is constituted of a silver sleeve 11. The conductance to this counter electrode, for example, is a copper or steel wire 12 with the insulation 13. For contacting thereof, the wire 12 is laid free ahead of the catheter tip, bent outwardly, and subsequently the silver sleeve 11 is slid over the free-lying wire end, and pressed fast. The contacting at the distal end may be effected through soldering or the application of a suitable plug member. The hollow space or chamber which is formed between the counter electrode and catheter tip due to the outward bending of the wire, is then closed off with a plastic material.

While there has been shown what is considered to be the preferred embodiment of the invention, it will be obvious that modifications may be made which come within the scope of the disclosure of the specification.

What is claimed is:

1. In an electrode for polargraphic/measurements in physiological media, in particular an oxygen electrode for measuring the oxygen tension in the human or animal body, including a noble metal cathode and an insulating material sheathing said cathode, a connector for an electrical power supply, indicating and processing unit being provided at the distal end of said cathode, an oxygen-pervious conductive membrane covering the proximal end of said cathode, and said proximal end of the cathode being conductively connected to an anode through said physiological medium, the improvement comprising: said noble metal cathode having the form of a conductor cable piece including at least one noble metal wire embedded in said insulating material and extending therethrough so as to constitute a conductor wire; a further body-compatible insulating material sheathing said insulated noble metal cathode, said further insulating material including at least two foils, said noble metal cathode being embedded between said foils, said foils being intimately connectablewith each other through thermal welding and pressable into circular shape through thermoplastic deformation.

2. An electrode as claimed in claim 1, said cathode having a diameter externally of said further insulating material in the range of 150 to 250 μm.

3. In an electrode for polargraphic measurements in physiological media, in particular an oxygen electrode for measuring the oxygen tension in the human or animal body, including a noble metal cathode and an insulating material sheathing said cathode, a connector for an electrical power supply, indicating and processing unit being provided at the distal end of said cathode, an oxygen-pervious conductive membrane covering the proximal end of said cathode, and said proximal end of the cathode being conductively connected to an anode through said physiological medium, the improvement comprising: said noble metal cathode having the form of a conductor cable piece including at least one noble metal wire embedded in said insulating material and extending therethrough so as to constitute a conductor wire; a catheter, said noble metal cathode being located on said catheter for direct insertion into the blood stream; said catheter including a through-channel for withdrawal of blood and tissue samples and for rinsing of the proximal cathode surface, said channel having the proximal end thereof at the rinsed cathode surface leading sideways from the catheter for purposes of rinsing.

4. In an electrode for polarographic measurements in physiological media, in particular an oxygen electrode for measuring the oxygen tension in the human or animal body, including a noble metal cathode and an insulating material sheathing said cathode, a connector for an electrical power supply, indicating and precessing unit being provided at the distal end of said cathode, an oxygen-pervious conductive membrane covering the proximal end of said cathode, and said proximal end of the cathode being conductively connected to an anode through said physiological medium, the improvement comprising: said noble metal cathode having the form of a conductor cable piece including at least one noble metal wire embedded in said insulating material and extending therethrough so as to constitute a conductor wire, a catheter, said noble cathode being located on said catheter for direct insertion into the blood stream, said catheter comprising at least one further metal member adjacent said noble metal wire for conductance towards an anode located on said catheter.

5. An electrode as claimed in claim 4, said metal member comprising a silver sleeve.

6. A method for polarographic measurements in physiological media, in particular an oxygen electrode for measuring the oxygen tension in the human or animal body, comprising the steps of sheathing a noble metal cathode with an insulating material connecting an indicating and processing unit to the distal end of said cathode, covering the proximal end of said cathode with an oxygen-pervious conductive membrane, connecting said proximal end of the cathode conductively to an anode through said physiological medium, forming said noble metal cathode as a conductor cable piece including at least one continuous noble metal wire embedded in said insulating material and extending therethrough so as to constitute a conductor wire cutting said cathode piece-by piece from said continuous noble metal wire, the pieces being then covered by said oxygen-pervious membrane, and connecting the pieces distally to electrical power supply lines.

7. A method as claimed in claim 6, said noble metal wire being constituted of a gold wire.

8. A method as claimed in claim 6, said noble metal cathode comprising a severed section of a noble metal wire-insulating cable.

9. A method as claimed in claim 6, comprising an insulating lacquer encasing said noble metal wire.

10. A method as claimed in claim 9, said insulating lacquer comprising polyurethane.

11. A method as claimed in claim 6, said noble metal wire having a diameter in the range of 10 to 100 μm.

12. A method as claimed in claim 11, said noble metal wire having a diameter of 60 μm.

13. A method as claimed in claim 6, said noble metal wire being recessed relative to the insulating material at the proximal end of said cathode.

14. A method as claimed in claim 13, said noble metal wire being recessed through etching.

15. A method as claimed in claim 13, including the step of positioning said oxygen-pervious membrane in the noble metal wire recess.

16. A method as claimed in claim 15, including the steps of positioning an electrolyte intermediate said noble metal wire and said membrane.

17. A method as claimed in claim 16, said electrolyte comprising as NaCl solution.

18. A method as claimed in claim 6, wherein said indicating and processing unit is directly connected to the distal end of said noble metal wire.

19. A method as claimed in claim 18, including the step of soldering connector conduits to said noble metal wire.

20. A method as claimed in claim 18, including the step of claming connector conduits to said noble metal wire.

21. A method as claimed in claim 6, including the step of locating said noble metal cathode on a catheter for direct insertion into the blood stream.

22. A method as claimed in claim 21, said noble metal cathode being a portion of said catheter.

23. A method as claimed in claim 21, including the step of sheathing said insulated cathode with a further body-compatible insulating material, said further insulating material forming said catheter.

24. A method as claimed in claim 21, said catheter including a high-tensile textile core.

* * * * *